United States Patent
Kim et al.

(10) Patent No.: US 9,807,987 B2
(45) Date of Patent: Nov. 7, 2017

(54) RECOMBINATION ACTIVATING GENE 2 GENE TARGETING VECTOR, PRODUCTION OF SCID-LIKE MINIATURE PIGS BY TALEN-MEDIATED GENE TARGETING AND USE THEREOF

(71) Applicants: KONKUK UNIVERSITY INDUSTRIAL COOPERATION CORP., Seoul (KR); THE CURATORS OF THE UNIVERSITY OF MISSOURI, Columbia, MO (US)

(72) Inventors: Jin-Hoi Kim, Seoul (KR); Deug-Nam Kwon, Seoul (KR); Randall S. Prather, Columbia, MO (US); Kiho Lee, Columbia, MO (US)

(73) Assignees: KONKUK UNIVERSITY INDUSTRIAL COOPERATION CORP., Seoul (KR); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/036,457

(22) PCT Filed: Nov. 13, 2014

(86) PCT No.: PCT/KR2014/010896
§ 371 (c)(1),
(2) Date: May 13, 2016

(87) PCT Pub. No.: WO2015/072760
PCT Pub. Date: May 21, 2015

(65) Prior Publication Data
US 2016/0366860 A1 Dec. 22, 2016

(30) Foreign Application Priority Data

Nov. 13, 2013 (KR) ........................ 10-2013-0137677

(51) Int. Cl.
| | | |
|---|---|---|
| A01K 67/027 | (2006.01) |
| C12N 15/877 | (2010.01) |
| C12N 15/90 | (2006.01) |
| C12N 5/074 | (2010.01) |
| C12N 15/85 | (2006.01) |

(52) U.S. Cl.
CPC ...... *A01K 67/0276* (2013.01); *A01K 67/0278* (2013.01); *C12N 5/0696* (2013.01); *C12N 15/8509* (2013.01); *C12N 15/8778* (2013.01); *C12N 15/907* (2013.01); *A01K 2217/075* (2013.01); *A01K 2227/108* (2013.01); *A01K 2267/0387* (2013.01); *C12N 2015/8536* (2013.01); *C12N 2501/40* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2506/025* (2013.01); *C12N 2510/00* (2013.01)

(58) Field of Classification Search
None
See application file for complete search history.

(56) References Cited

U.S. PATENT DOCUMENTS

2012/0222143 A1   8/2012   Fahrenkrug et al.

FOREIGN PATENT DOCUMENTS

KR   10-2004-0074108 A   8/2004

OTHER PUBLICATIONS

Huang, J. et al., "RAG1/2 knockout pigs with severe combined immunodeficiency", J. Immunol., 2014, vol. 193: pp. 1496-1503.*
Rebecca H. Buckley, "Molecular Defects in Human Severe Combined Immunodeficiency and Approaches to Immune Reconstitution," Annu. Rev. Immunology 2004, vol. 22, pp. 625-655.
Jeffrey J. Whyte et al., "Genetic Modifications of Pigs for Medicine and Agriculture," Molecular Reproduction & Development, 2011, vol. 78(10-11), pp. 879-891.
Anna Villa et al., "Omenn Syndrome: A Disorder of Rag 1 and Rag 2 Genes," Journal of Clinical Immunology, 1999.
Yoichi Shinkai et al., "RAG-2-Deficient Mice Lack Mature Lymphocytes Owing to Inability to Initiate V(D)J Rearrangement," Cell, 1992.
Masahito Watanabe et al., "Generation of Interleukin-2 Receptor Gamma Gene Knockout Pigs from Somatic Cells Genetically Modified by Zinc Finger Nuclease-Encoding mRNA," PLOS ONE, vol. 8, Issue 10, Oct. 2013.
Hyojin Kim et al., "Magnetic Separation and Antibiotics Selection Enable Enrichment of Cells with FN/TALEN-Induced Mutations," PLOS ONE, vol. 8, Issue 2, Feb. 2013.
Jun Song et al., "Generation of RAG 1- and 2-deficient rabbits by embryo microinjection of TALENs," Cell Research, 2013, vol. 23, pp. 1059-1062.
Kiho Lee et al., "Engraftment of human iPS cells and allogeneic porcine cells into pigs with inactivated RAG2 and accompanying severe combined immunodeficiency," PNAS, vol. 111, No. 20, May 20, 2014.
Daniel F. Carlson et al., "Efficient TALEN-mediated gene knockout in livestock," PNAS, vol. 109, No. 43, Oct. 23, 2012.
Extended European Search Report in European Patent Application No. 14862841.5, dated Mar. 24, 2017.

* cited by examiner

*Primary Examiner* — Michael Burkhart
(74) *Attorney, Agent, or Firm* — Baker & Hostetler LLP

(57) ABSTRACT

There are provided to a Rag-2 (Recombination activating gene 2) gene targeting vector, a method for producing SCID-like miniature pigs introduced with the vector, and a use thereof.

10 Claims, 15 Drawing Sheets

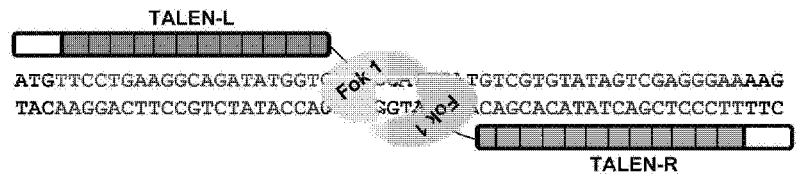
FIG. 1A
FIG. 1B
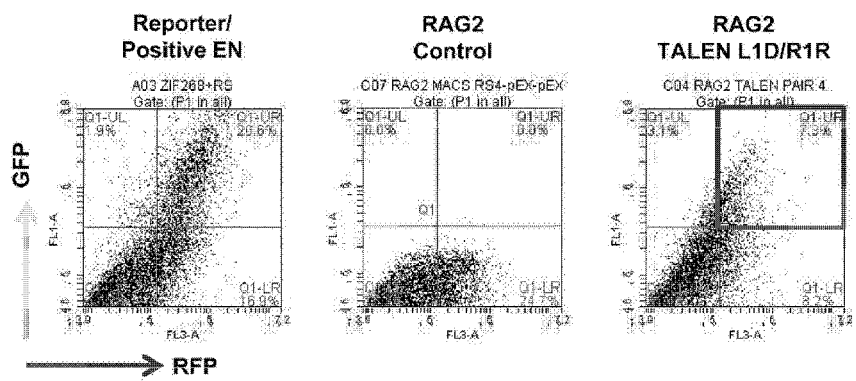
FIG. 1C
*RAG2* monoallelic
TTCCTGAAGGCAGATATGGTCATTCCATTGATGTCGTGTATAGTCGAGGGAA
TTCCTGAAGGCAGATATGGTC ---- CCATTGATGTCGTGTATAGTCGAGGGAA
*RAG2* biallelic
TTCCTGAAGGCAGATATGGTC ---- CCATTGATGTCGTGTATAGTCGAGGGAA
TTCCTGAAGGCAGATATG--------------------------GTCGTGTATAGTCGAGGGAA
FIG. 1D

RAG2

FIG. 9

RECOMBINATION ACTIVATING GENE 2 GENE TARGETING VECTOR, PRODUCTION OF SCID-LIKE MINIATURE PIGS BY TALEN-MEDIATED GENE TARGETING AND USE THEREOF

CROSS-REFERENCE TO RELATED APPLICATIONS

This application is the National Stage of International Patent Application No. PCT/KR2014/010896, filed Nov. 13, 2014, which claims the benefit of Korean patent application number KR 10-2013-0137677, filed Nov. 13, 2013, the disclosures of which are incorporated herein by reference in their entireties.

SEQUENCE LISTING

The instant application contains a sequence listing which has been submitted electronically in ASCII format and is hereby incorporated by reference in its entirety. The ASCII copy, entitled 087248.003360_SL.txt, was created on Aug. 31, 2016, is 26,088 bytes in size.

TECHNICAL FIELD

The present invention relates to a Rag-2 (Recombination activating gene 2) gene targeting vector, a method for producing SCID-like miniature pigs introduced with the vector, and a use thereof.

BACKGROUND ART

A severe combined immunodeficiency (hereinafter, referred to as "SCID") occurs in humans (Buckley, R. H. *Annual review of immunology* 22, 625-655 (2004)). However, a medicine for treating the SCID is as yet undeveloped due to the limited animal model reflecting a human SCID type. A pig has physiological properties that are very similar to those of humans and a higher similarity as compared with rodent models, which has been designed to copy many human diseases (Whyte, J. J. & Prather, R. S. *Molecular reproduction and development* 78, 879-891(2011)). Therefore, a SCID pig may be representative of the models that have been designed to copy human diseases. In addition, the SCID models may be used for a cancer research, cell transplantation, and drug development study.

A recombination activating gene 2 (hereinafter, referred to as "RAG2") is involved in the autosomal-related SCID diseases in humans (Villa, A., Santagata, S., Bozzi, F., Imberti, L. & Notarangelo, L. D. *Journal of clinical immunology* 19, 87-97 (1999)). A mutation in the RAG2 causes damaged B and T cells, and since the RAG2 is important for V(D)J rearrangement, it destroys an adaptive immune system (Shinkai, Y. et al. *Cell* 68, 855-867 (1992)).

PATENT LITERATURE

Patent Literature 1: Korean Patent Laid-open Publication No. 1020040074108

DISCLOSURE

Technical Problem

In order to solve the conventional problems, an object of the present invention is to provide an effective method for producing a genetic engineering pig causing a SCID phenotype.

Technical Solution

In order to achieve the above object, the present invention provides a method for producing SCID-like miniature pigs having recombination activating gene (RAG) 2-allelic mutation, in which the method includes inducing an allelic mutation by treating a transcription activator-like effector nuclease (TALEN) to a TALEN-recognizing sequence region as set forth in SEQ ID NO. 1 in Chromosome 2 of a pig (*Sus scrofa*), and producing the mutant embryos by using the cells with the induced allelic mutation for somatic cell nuclear transplantation.

According to an embodiment of the present invention, it is preferable to induce the allelic mutation by transfecting relevant cells using the TALEN in a type of the vector encoding a TAL effector-DNA nuclease, but the present invention is not limited thereto.

In addition, the present invention provides SCID-like miniature pigs having a recombination activating gene 2-allelic mutation, which is produced by the producing method of the present invention.

In addition, the present invention provides a method for sorting the RFP, GFP, and H-2KK-positive cells as the recombination activating gene (RAG) 2-targeted cells, in which the method includes introducing the vector encoding a TAL effector-DNA nuclease capable of inducing the mutations of the relevant gene region or the surrounding sites by recognizing the TALEN-recognizing sequence as set forth in SEQ ID NO. 1 in Chromosome 2 of a pig (*Sus scrofa*), and a reporter vector including a monomeric red fluorescent protein (RFP) gene, a targeting sequence of the programmable nuclease as set forth in SEQ ID NO. 1, an enhancer green fluorescent protein (GFP) gene and a H-2KK gene, together to the cells.

According to an embodiment of the present invention, it is preferable to perform the detection of the H-2KK by an antibody, but the present invention is not limited thereto.

According to another embodiment of the present invention, it is preferable to detect the expressions of the RFP and GFP by a flow cytometry, but the present invention is not limited thereto.

In addition, the present invention provides the cells with the induced allelic mutation by inducing the allelic mutation by treating a transcription activator-like effector nuclease (TALEN) to a TALEN-recognizing sequence region as set forth in SEQ ID NO. 1 in Chromosome 2 of a pig (*Sus scrofa*).

The cells were deposited at the gene bank (Korean Collection for Type Cultures) in Korea Research Institute of Bioscience and Biotechnology, located at Yuseong-gu, Daejeon, South Korea, on Oct. 2, 2013, at Accession No.: KCTC 12496BP.

Hereinafter, the present invention will be described.

In the present invention, the present inventors report an effective method for producing two types of the genetic engineering pig causing a SCID phenotype by using a TALEN (transcription activator-like effector nuclease)-mediated gene targeting including a somatic cell nuclear transplantation (SCNT).

In order for targeting a pig RAG2, the specific TALENs were designed and synthesized in Toolgen (Seoul, South Korea). The TALENs were designed to cause mutations on Exon 2 of RAG2 (FIG. 1a). A reporter containing TALEN recognition sites was used to identify cells that were properly expressing TALEN sets (FIGS. 3 and 1b). The activity of the designed TALENs was validated by introducing the TALEN sets with a reporter into HEK 293T cells (FIG. 1c).

After validation, the constructs coding for TALENs and a reporter were introduced into pig fibroblast cells by electroporation. After 48 hours the cells were sorted for GFP positive cells (FIG. 4), and plated in 96-well plates; a single cell in a well. After 10 days, cells were passaged and half of the cells were used for genotyping. Sequencing of small PCR fragments (around 400 bp) flanking the predicted TALEN cutting 52 sites revealed the presence of indels from the TALENs in RAG2 groups; total of 57 colonies were screened for RAG2 (see primer information listed in Table 1). The efficiency of gene targeting was 42.1% (24/57) for RAG2 (FIG. 1d). We observed 14% (8/57) biallelic modification in cells induced with RAG2 TALENs. The efficiency of gene targeting was 42.1% (24/57) with respect to RAG2. The TALENs used in the present invention were specific to the targeted regions, and therefore we did not observe any off-target cutting (FIG. 6 and Table 2). The targeting confirmed cells were used for somatic cell nuclear transfer (SCNT) (FIG. 7).

Mutant embryos were produced by SCNT and 733 embryos were transferred to four surrogate gilts that resulted in establishment of four day 25 pregnancies that all gestated to term. 13 RAG2 mutants were born, in addition to 3 still born RAG2 mutants (FIG. 1d).

Interestingly, the present inventors produced RAG2 mutants harboring either mono- or biallelic modification of RAG2 from a single cell colony. Specifically, all RAG2 genetically engineered pigs shared the same modification on one allele but some pigs had another modification on the other allele. The monoallelic mutants have a deletion of a single amino acid and one amino acid replacement due to the loss of three nucleotides (RAG2+/Δ140, S141H), and the biallelic mutants have the same modification and a formation of premature stop codon on the other allele because of the deletion of fourteen nucleotides (RAG2Δ140, S141H/Δ140-527).

Genotyping of RAG2 biallelic mutants (RAG2Δ140, S141H/Δ140-527) suggested that the mutants may lack functional RAG2, as the missing and replaced amino acids are highly conserved in various species of RAG2 at a beta propeller region (FIG. 9).

On day 17, wildtype, RAG2 monoallelic and biallelic mutants were sacrificed and necropsied. While the thymus was not detected in the RAG2Δ140, S141H/Δ140-527 pigs, the thymus having the similar size as the wild type was detected in the RAG2+/Δ140, S141H pigs (FIG. 2a). In addition, the size of the spleen of the biallelic mutant was smaller than that of the control pigs (FIGS. 2b and 2c). This results are in concordance with the results observed in mice, and it is suggested that the immunological deficiency is detected in the RAG2+/Δ140, S141H pigs.

Immunohistochemistry (IHC) and hematoxylin and eosin (H & E) staining from RAG2Δ140, S141H/Δ140-527 pig spleen revealed the white pulp was markedly hypoplastic with lack of germinal center and periarteriolar lymphoid sheath (PALS) formation and rare B and T cells throughout (FIGS. 2d and 10). On the other hand, the levels of B and T cells derived from the RAG2+/Δ140, S141H pigs were normal. Similarly, from the flow cytometry performed by using splenic leukocyte, it is shown that mature B and T cells are insufficient in the RAG2Δ140, S141H/Δ140-527 pigs (FIG. 2e). During monitoring for 4 weeks, the present inventors observed the differences of weight gains in the wildtype, RAG2 monoallelic mutant, and biallelic mutant. All the pigs exhibited the similar weight gains for 2 weeks, but the weights of the RAG2Δ140, S141H/Δ140-527 pigs were plateaued (FIG. 20. After 4 weeks, the weight of the RAG2 biallelic mutant was smaller than that of the monoallelic mutant. These animals were grown in a non-specific sterile (SPF) housing, and the final RAG2Δ140, S141H/Δ140-527 pig died at 29-day. The remaining RAG2 monoallelic mutants were healthy and normally grown.

In the present invention, the present inventors found that the SCID pigs prepared by a SCNT can be effectively produced by a TALEN-mediated gene targeting. By using a reporter vector having a TALEN construct, the mutation could be induced at a high rate.

Unlike conventional gene targeting where a targeting vector gets integrated into the genome, this approach allows us to produce genetically engineered pigs without any signature left in the genome.

The genetic engineering pigs produced according to the present invention can be used as a model for a SCID research, which including a first pig model capable of exhibiting a Omenn syndrome in humans (the pigs can be obtained from National Swine Resource and Research Center, USA, http://nsrrc.missouri.edu/).

To test whether the RAG2Δ140, S141H/Δ140-527 pigs would support proliferation and differentiation of human iPSCs, we injected pigs s.c. with cells from a potentially pluripotent cell line that had been generated from human umbilical cord fibroblasts by reprogramming with nonintegrating plasmid vectors to determine whether the cells would give rise to teratomas. Before injection, the cells had been alkaline phosphatase-positive and expressed the pluripotent markers [POU class 5 homeobox 1 (POU5F1), Nanog homeobox (NANOG), stage specific embryonic antigen 3 (SSEA-3)] (FIG. 12 c-e). Because the RAG2Δ140, S141H/Δ140-527 pigs were immunocompromised, the second group of newly born piglets used for this experiment were housed independently, and all personnel contacting the animals wore protective personal equipment (PPE) in an attempt to minimize pathogen exposure. On day 1 of the experiment, either 5 or 10 million cells were injected s.c. close to the base of the right ear and on the animal's left flank (biallelic pigs, n=3; monoallelic pigs, n=2). One biallelic mutant pig died of unknown cause on day 7 without showing any sign of tumor formation, but the other two developed tumors at each of the two injection sites. Tumor formation occurred rapidly compared with the usual time span of many weeks in SCID mice. A palpable tumor was observed by day 12 below the ear site of one biallelic mutant pig that had received an injection of 10 million cells (FIG. 14a and FIG. 13). By day 28, this tumor was capsulated, solid, and partly cystic (size, 3.4×2.5 cm; weight, 3.6 g) (FIG. 14 a and b), and appeared to have caused no ill effects to the host. At necropsy, it was dissected into five pieces, and sections of tissues were examined by H&E staining. Each tumor section contained a disorganized mixture of tissues (FIG. 14c). Striated muscle (mesoderm) (FIG. 14 c and e) was particularly evident and formed randomly distributed islands of tissue throughout the tumor. Various other areas comprised epithelium-like cells organized into glandular-like structures. They included secretoryepithelia: i.e., epithelium with goblet cells (endoderm) (FIG. 4d) and neural epithelium (ectoderm) (FIG. 4f). General histological assessments were confirmed by immunohistochemical analysis with antibodies against CTNNB1 and VWF [-catenin and von Willebrand factor (VWF): endoderm] (FIG. 4 g and j), DES and ACTG2 (desmin and smooth muscle actin: mesoderm) (FIG. 4 h and k), and GFAP and ENO2 (glial fibrillary acidic protein and neuron-specific enolase: ectoderm) (FIGS. 4 i and l). Cells positive for the markers of hematopoietic lineage and potentially pluripotent cells were also noted (FIG. 17). The second biallelic mutant pig formed slower-growing, smaller tumors (0.75 g and 0.35 g) at the ear site (where 5 million cells were injected) and flank (10 million cells injected) by 7.5 wk. An additional tumor was found in the peritoneal cavity of the second pig near the injection site on the left flank. Proportionately less muscle tissue and more cystic structures (FIG. 15a) were observed in tumors from the second pig, but derivatives of all three germ layers were still present (FIG. 15 b-d). These differences in teratoma characteristics cannot be attributed to the iPSC source because the same cells were used for each pig. The tumors were also clearly of human and not porcine origin, as amplicons from human-specific MFN1 (mitochondrial mitofusin-1) were successfully amplified from the DNA of the human iPSC line and its derived teratoma but not from DNA of the mutant pig (FIG. 16). To explore whether RAG2Δ140, S141H/Δ140-527 pigs could accept allogeneic pig cells, we injected what we have inferred previously to be porcine trophoblast stem cells, which, in nude mice, had given rise to solid tumors comprised largely of packed epithelial layers, with islands of striated muscle tissue near the periphery. These same cells provided a somewhat similar, encapsulated tumor in pigs by day 17. This tumor, like the ones from mouse, was comprised predominantly of layers of epithelial tissue.

Advantageous Effects

The pigs exhibiting the phenotype of a severe combined immunodeficiency (SCID) may offer assistance to a stem cell therapy, a cancer research, and the development of heterologous graft. The present inventors describe the productions of two types of SCID pigs and RAG2 knockout through a TALEN-mediated targeting. The RAG2 monoallelic mutation causes an immunological deficiency verified by the hypoplasia of white pulp exhibiting the non-detected thymus and the lack of B and T cells.

DESCRIPTION OF DRAWINGS

FIG. 1a, FIG. 1b, FIG. 1c, and FIG. 1d illustrate schematic diagrams illustrating the production of SCID pigs using TALENs, of which (FIG. 1a) shows TALEN-mediated knockout of RAG2 (SEQ ID NOs: 20-21, respectively, in order of appearance), (FIG. 1b) shows a donor reporter vector including a TALEN-recognizing domain, in which the cleavage of the TALEN-recognizing domain in the donor reporter vector induces the expression of GFP, (FIG. 1c) shows the confirmation of TALENs designed in vitro, in which the expression of the GFP may be detected only when TALENs are transfected along with the donor reporter gene in a HEK 293T cell, and (FIG. 1d) shows the genotype of the genetic engineering pigs (SEQ ID NOs: 1, 22 and 22-23, respectively, in order of appearance).

(FIG. 4a) There was high coexpression of RFP and GFP after 48 hours post transfection. (FIG. 4b) Boxes below the arrows indicate GFP positive cells. Top 10% cells expressing strong GFP were sorted and placed in 96-well plates. Range of GFP positive cells were from 23.0% to 38.0% (scale bar=20 μm).

Figure 9:
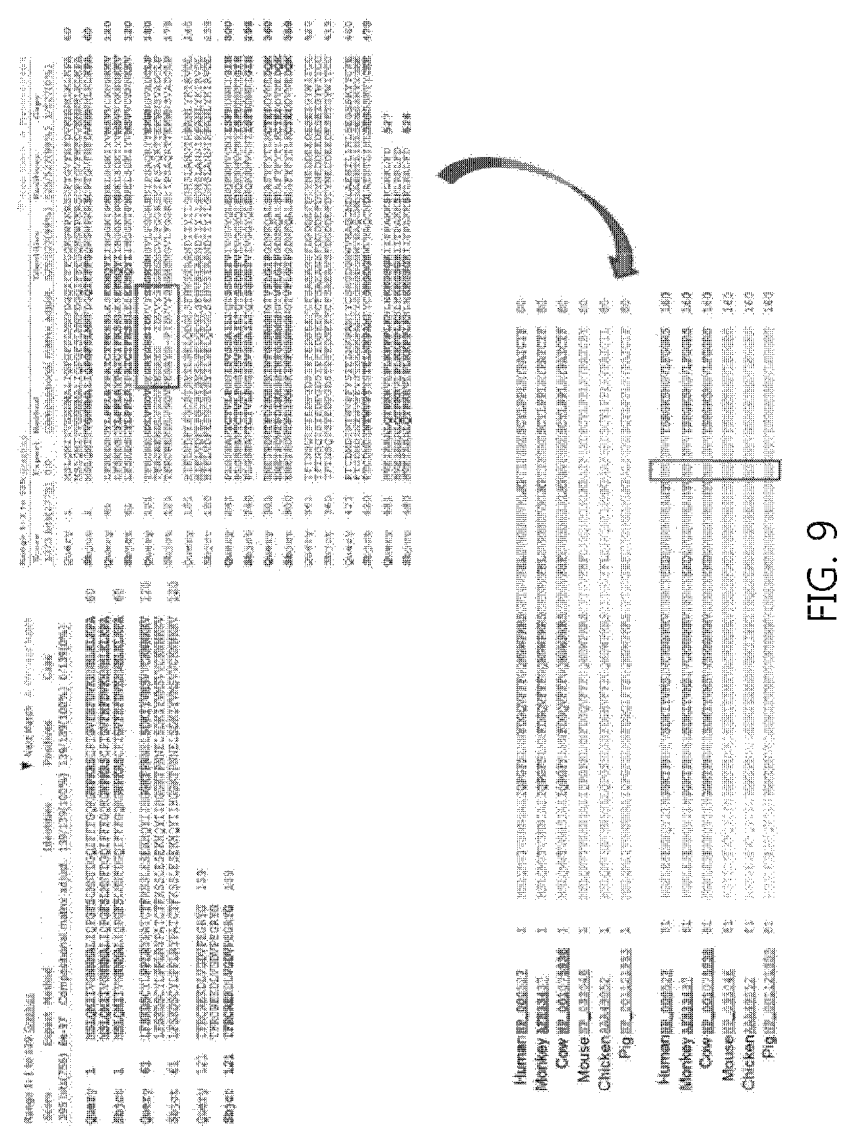

FIG. 9 illustrates mutation on conserved domain of RAG2. (a) Predicted protein sequence from RAG2 mutation. Deletion of 14 bp results in a premature stop codon. (b) Predicted protein sequence from RAG2 mutation. Loss of 3 base pair resulted in a deletion and a mismatch of one amino acid. (c) The modified amino acids are highly conserved among different species. This suggests that the mutants are likely to have nonfunctional RAG2. FIG. 9 discloses the first alignment as SEQ ID NOs: 34 and 34, the second alignment as SEQ ID NOs: 35 and 36 and the third alignment as SEQ ID NOs: 37-42, all respectively, in order of appearance.

BEST MODE

Figure 2A:
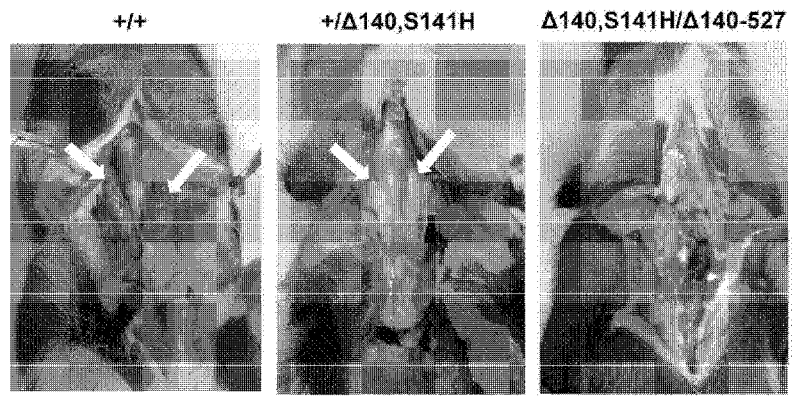
FIG. 2a, FIG. 2b, FIG. 2c, FIG. 2d, FIG. 2e, and FIG. 2f illustrate the characteristics of the SCID pigs exhibiting a Omenn syndrome, of which (FIG. 2a) shows there is no thymus in RAG2 biallelic mutant, (FIG. 2b) shows the sizes of the spleens of wildtype, mono and biallelic mutants pigs, in which the RAG2 biallelic mutant has the smaller spleen as compared with the wildtype and monoallelic mutant, (FIG. 2c) shows the weights of the spleens of the wildtype, mono and biallelic mutants pigs, in which the RAG2 biallelic mutant has lighter spleen as compared with others, (FIG. 2d) shows the SCID phenotype in the biallelic mutant pig, in which according to the IHC staining of CD79A (B cell) and CD3 (T cell) in the spleen, it can be confirmed that the RAG2 biallelic mutant have rare B and T cells; the B cells are observed around germinal center in the wildtype and monoallelic mutant; and the T cells are mainly observed in PALS; but the number of B or T cells in the biallelic mutant is significantly decreased, and these cells are not observed in the group, and are only rarely observed as an individual cell in the splenic stroma, (FIG. 2e) Flow cytometry result showing a significant reduction in B (CD21) and T (CD3) cells in the spleen of RAG2 biallelic mutant compared to wildtype pig. Only 2-3% of splenocytes from biallelic mutants were positive for B cell or T cell markers, roughly equivalent to the fluorescence attained with an isotype control antibody and (FIG. 2f) Body weight of control, monoallelic, and biallelic mutant pigs. RAG2 biallelic mutants stop gaining weight after two weeks.
Figure 2B:
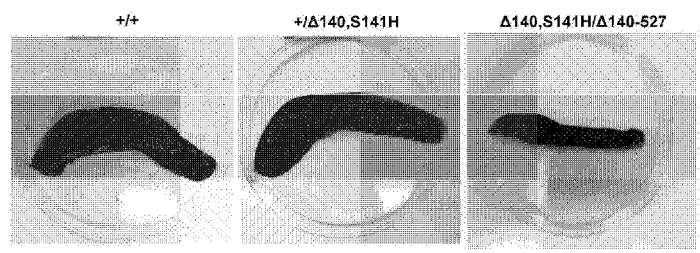
Figure 2C:
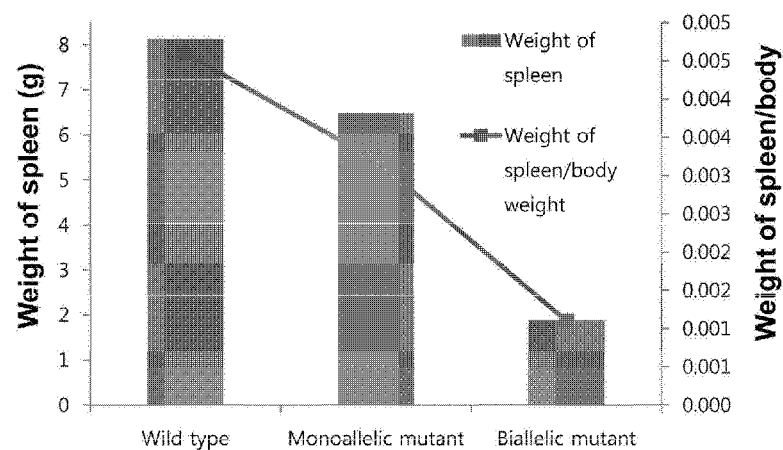
Figure 2D:
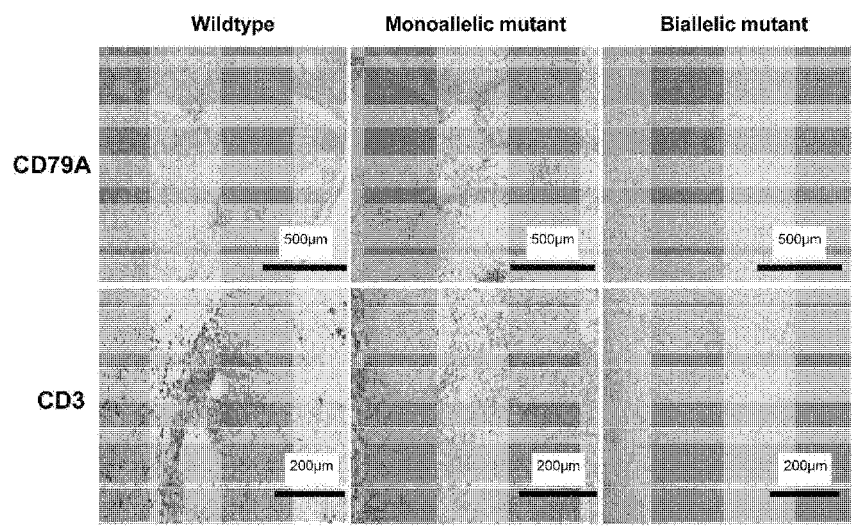
Figure 2E:
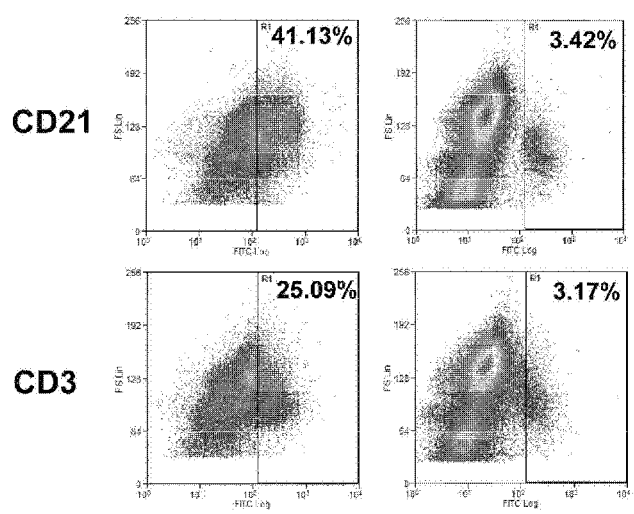
Figure 2F:
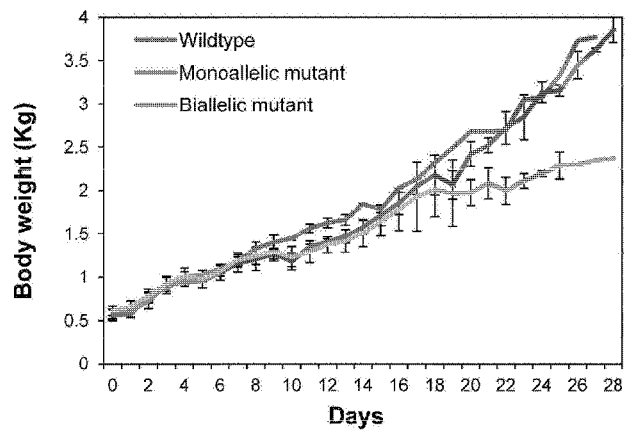
Figure 3:
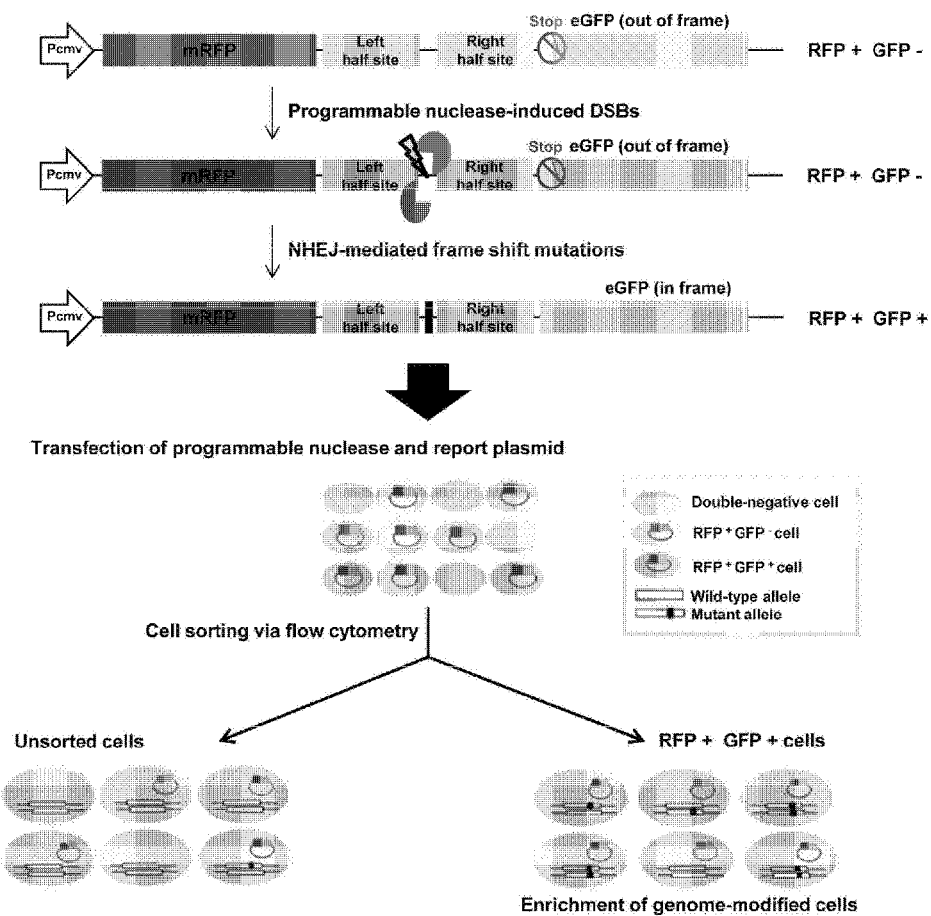
FIG. 3 illustrates construction of surrogate reporter vector for enrichment of targeted cells by TALENs. (a) The reporter vector consists of the monomer RFP gene, the programmable nucleases target sequence (left and right half-sites), the enhancer GFP and the H-2KK gene (upper panel of a). If GFP and H-2KK sequence are out of frame because of the absence of programmable nuclease activity, only the RFP gene is expressed. When a double-strand break is introduced into the target sequence by programmable nucleases, the break is repaired by non-homologous end-joining (NHEJ), which often causes frame shift mutations. Such mutations can render GFP into in frame with RFP, inducing the expression of the mRFP–eGFP–H-2KK fusion protein (low panel of a). (b) Schematic illustrates enrichment of nuclease-induced mutations in mRFP+eGFP+H-2KK+ cells sorted by two systems: magnetic separation by H-2KK antibody and flow cytometry by RFP and GFP expression. Within cells, reporter plasmids and chromosomal target loci are illustrated. Mutations are shown as black spots in the figure.
Figure 4A:
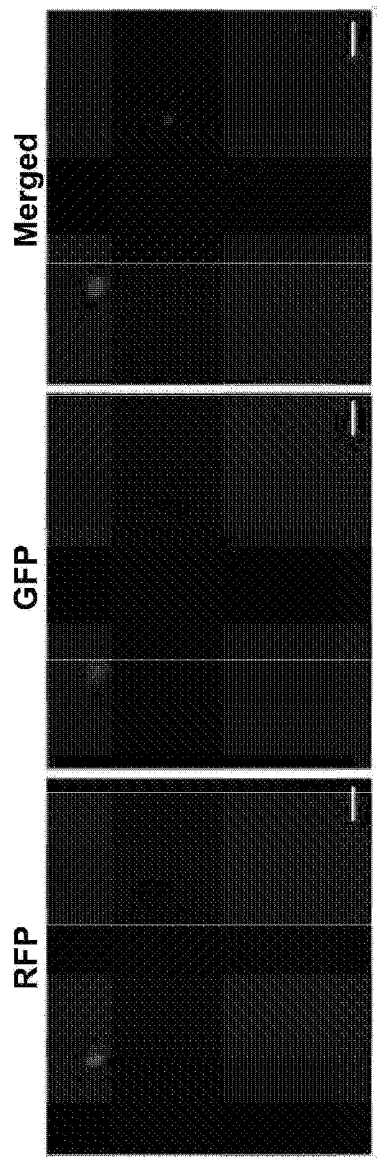
FIG. 4a and FIG. 4b illustrate FACS sorting of GFP positive cells after introducing TALENs.
Figure 4B:
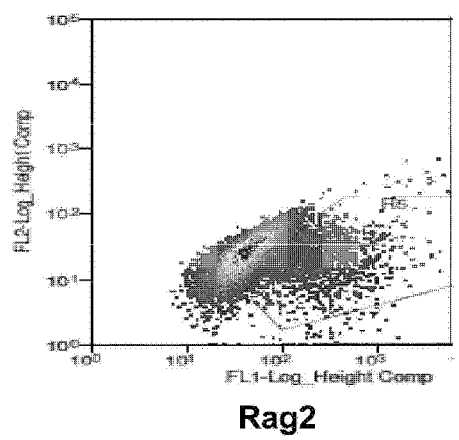
Figure 5:
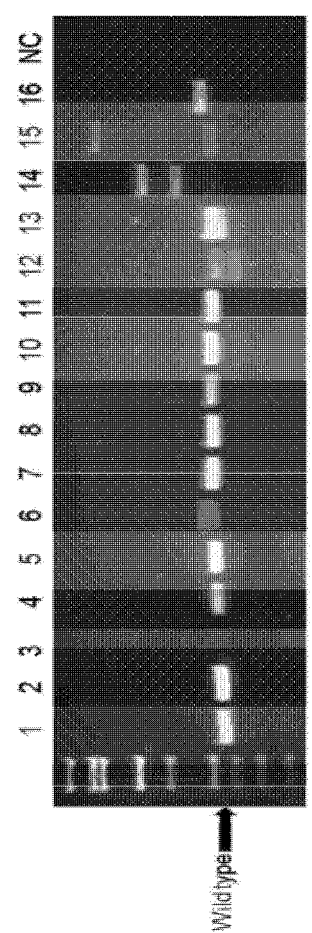
FIG. 5 illustrates Mono- and biallelic modification of RAG2 using TALEN. PCR products flanking TALEN binding site are shown. In several occasions, there was an absence of PCR band at wild type size indicating clear biallelic modification of RAG2 (Lane 14). The PCR products were loaded on a 2.0% agarose gel.
Figure 6:
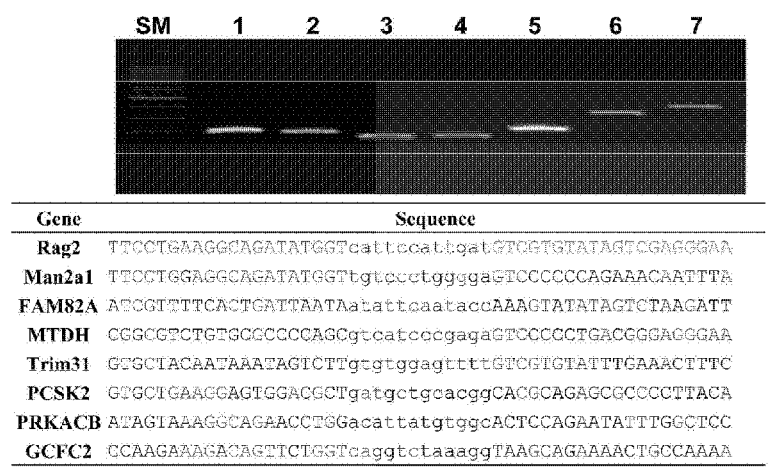
FIG. 6 illustrates Off-target analysis of RAG2 genes from RAG2 mutated pigs. (a) Upper) Surveyor nuclease digest of heteroduplex DNA revealed no additional off-target mutations at the 7 loci with highest homology to RAG2 gene; SM: size marker, lane 1: MAN2A1; 2: FAM82A; 3: MTDH; 4: TRIM31; 5: PCSK2; 6, PRKACB; 7, GCFC2. Bottom) Genes and sequence homologies of RAG2 related sequence to exclude off-target mutations (SEQ ID NOs: 24-31, respectively, in order of appearance). Upper case: TALEN binding sites; lower case; TALEN cut site; homolog base pairs in red.
Figure 7:
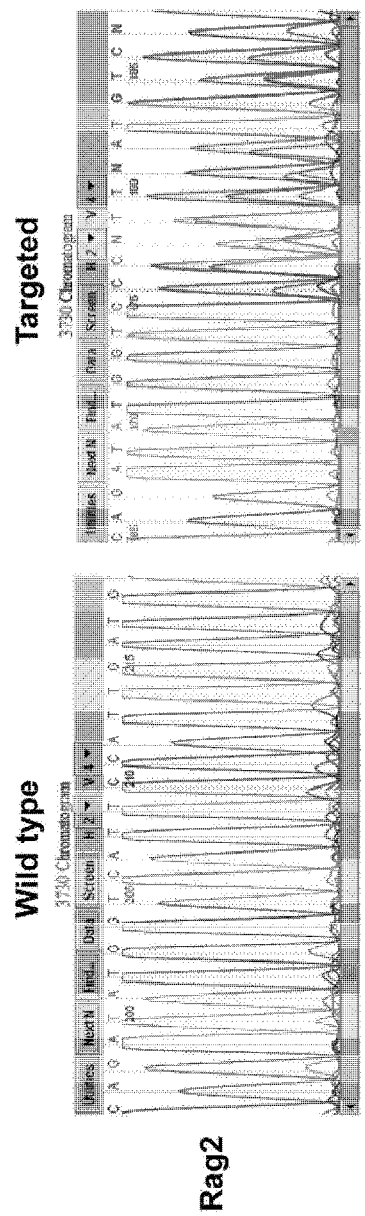
FIG. 7 illustrates PCR sequencing results to identify candidate cell colonies for SCNT (SEQ ID NOs: 32 and 33, respectively, in order of appearance). Introducing TALENs induced polymorphisms near TALEN binding sites due to NHEJ. Types of polymorphisms were analyzed then cell colonies were used for SCNT.
Figure 8:
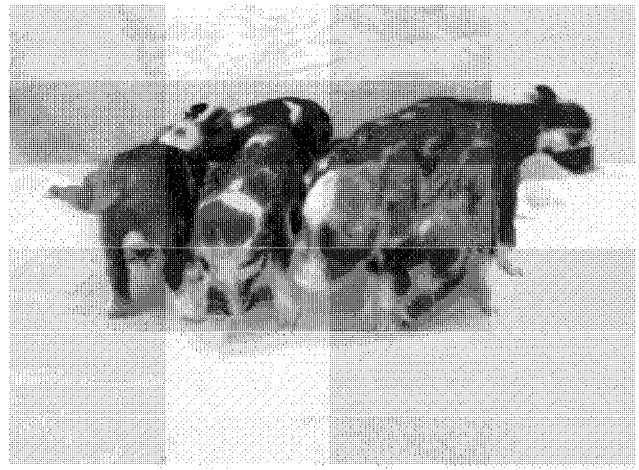
FIG. 8 illustrates the images of the SCID pig models produced according to the present invention, in which the genetic background of the pigs is the Minnesota miniature pigs.
Figure 10:
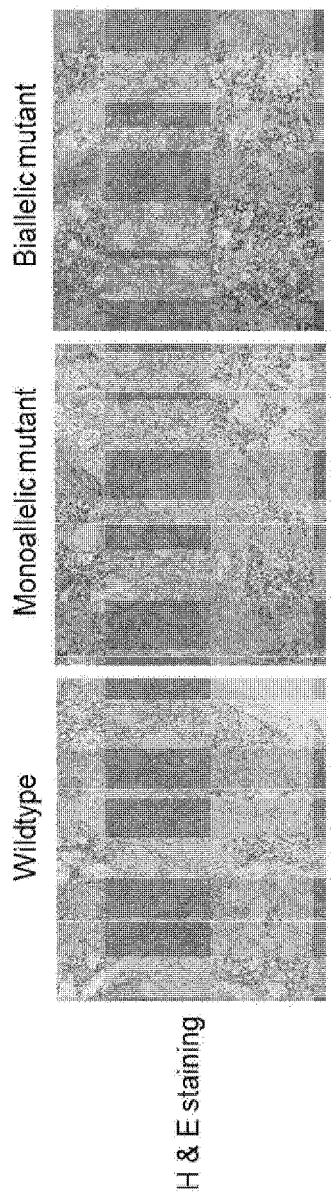
FIG. 10 illustrates developmental defects of spleen in RAG2 double mutants. H&E stained sections from biallelic mutants revealed a marked white pulp hypoplasia with lack of a germinal center and periarteriolar lymphoid sheath (PALS) formation.
Figure 11:
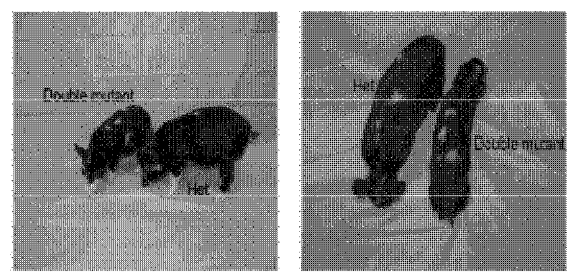
FIG. 11 illustrates the images of RAG2 bi- and mono-allelic mutants after four weeks. RAG2 biallelic mutants stopped gaining weight after two weeks. After four weeks, there is visible difference in phenotype between RAG2 bi- and mono-allelic mutant pigs.
Figure 12:
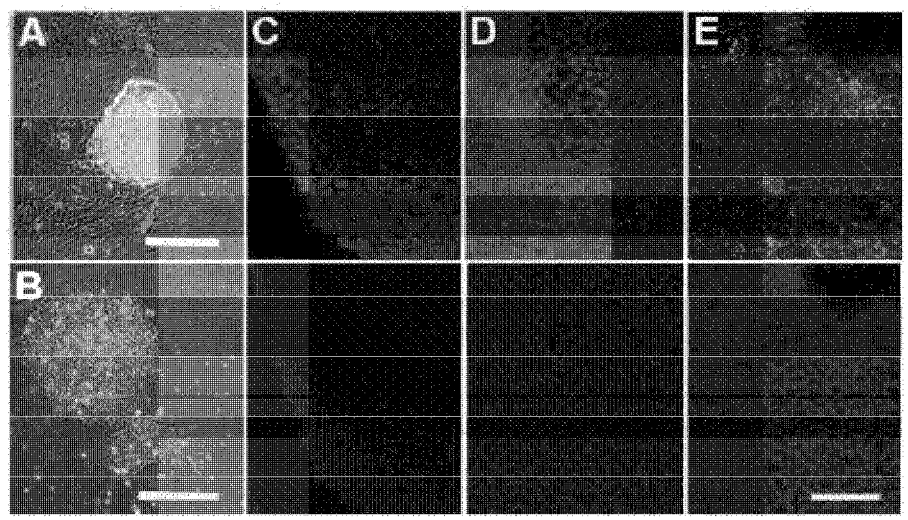
FIG. 12 illustrates Generating human iPSC with episomal plasmids. (A) Phase contrast image of an iPSC colony at 14 days after the plasmid transfections to umbilical cord outgrowth. (B) Image of the isolated iPSC colonies on feeder-free culture conditions. (C-E) Pluripotent nuclear protein POU5F1 (C), NANOG (D) and cell surface molecule SSEA-4 (E) were expressed in the cells. Lower panels show nuclear staining with 4',6-diamidino-2-phenylindole (DAPI). Bars=200 µm in A & B, and 100 µm in E.
Figure 13:
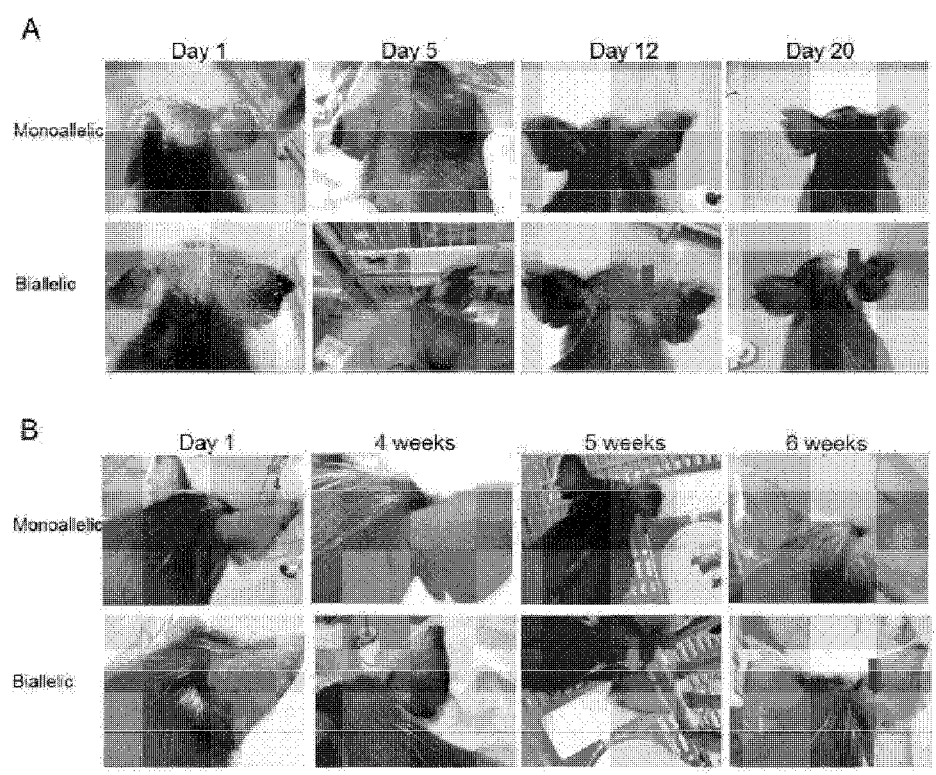
FIG. 13 illustrates Progression of the growth of teratomas in RAG2 mutant pigs. (a) Pigs received 10 million cells. A growth was detected on the injection site around 12-14 days post-injection. (b) Pigs received 5 million cells. A growth was detected after 5 weeks post-injection. The arrows indicatesites of potential teratoma growth. No growth was observed from monoallelic RAG2 mutants.
Figure 14:
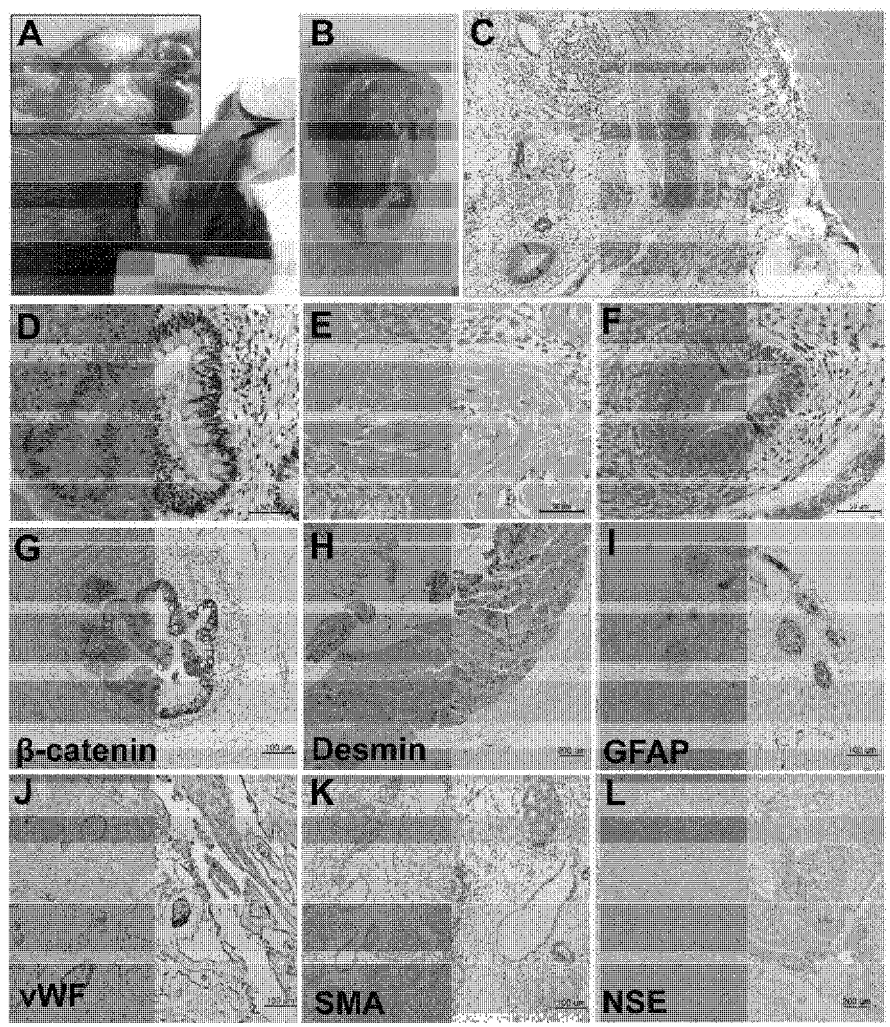
FIG. 14 illustrates Teratoma formation in RAG2Δ140, S141H/Δ140-527 pigs. (A) External view of a tumor at day 16 (Upper Inset, red arrow) and 4 wk (Lower) after injection of 10 million cells below the ear. (B) Gross morphology of the capsulated tumor collected from the injection site. (C-O) Histological examination of the tumors. Sections were stained by H&E (C-F collected from the tumor at the ear site) and for a range of diagnostic antigen immunohistochemistry (G-O). C is viewed at a lower magnification of the tissues. (Scale bar: 200 µm) (M and N) Cells positive for hematopoietic markers were present within the teratoma. (O) Presence of undifferentiated POU5F1+ cells in the teratoma (green fluorescence, POU5F1; blue, DAPI stain for DNA). (Scale bar: 200 µm)
Figure 15:
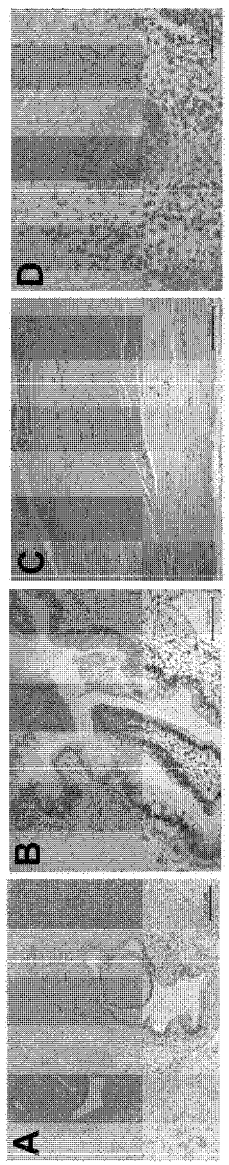
FIG. 15 illustrates Histological analysis of the teratoma that formed on the lateral flank area of the second RAG2Δ140, S141H/Δ140-527 pig, where tumor progression was relatively slow. The tumor section contained a disorganized mixture of tissues with proportionately less muscle tissue and more cystic structures than observed in the teratomas of the first mutant pig (a) Low magnification view of a section of the teratoma; (b-d) Representative sections illustrating the presence of the three germ layers (B endoderm; C mesoderm; D ectoderm) Bar=100 µm.
Figure 16:
FIG. 16 illustrates Human origin of the teratoma. A fragment of human specific mitochondrial mitofusin 1 (MFN1) was amplified by using PCR. Expected size of the human amplicon was 236 bp. 1, genomic DNA from human iPSC #1 line; 2, genomic DNA from human iPSC #2 line; 3, genomic DNA from RAG2Δ140, S141H/Δ140-527 pig used as the recipient; 4, genomic DNA from the teratomas; (−), − negative control (no DNA).
Figure 17:
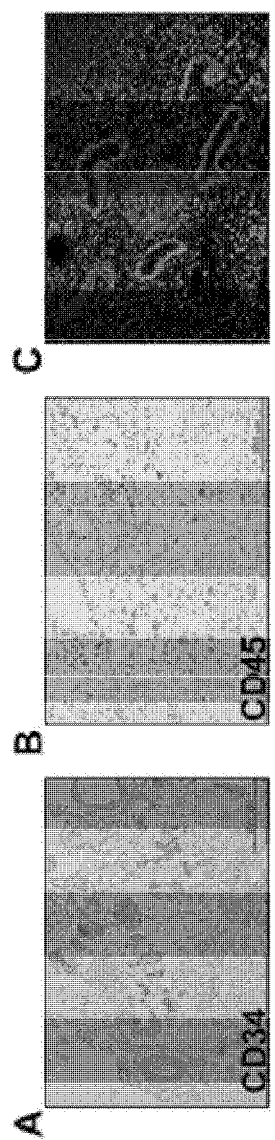
FIG. 17 illustrates Staining using hematopoietic markers. (a, b) Cells positive for hematopoietic markers were present within the teratoma. (c) Presence of undifferentiated POU5F1+ cells in the teratoma (green fluorescence, POU5F1; blue, DAPI stain for DNA).

Hereinafter, the present invention will be described in more detail with reference to the non-limited Examples. However, the following Examples are only for illustrating the present invention, but it should be understood that the range of the present invention is not limited to the following Examples.

All the animals and experiments used for the present invention received an approval from Animal Ethics Committee located in University of Missouri.

Example 1: Cell Transfection and Gene Targeting

For gene targeting, 2-3 million cells were transfected with TALEN constructs with a reporter vector; 2 µg of each construct per million cells. The cells were electroporated with the constructs at 490 V, 1 msec, 3 pulses using a BTX Electro Cell Manipulator (Harvard Apparatus, Holliston, Mass.). The cells were plated in T75 flasks for 48 hours then sorted for GFP positive cells using Beckman Coulter MoFlo XDP. The sorted cells were plated in 96-well plates. After ten days, half of the cells were used for genotyping.

To investigate the presence of indels after introducing TALENS, a fragment of genomic DNA flanking TALEN cutting site was amplified by PCR. Genomic DNA from cultured cells was isolated using cell lysis buffer then the genomic DNA was used for the PCR. PCR conditions for the amplification was initial denaturation of for 2 min at 95° C. followed by 32 cycles of 30 sec at 94° C. for denaturation, 30 sec at 55° C. for annealing, and 30 min at 72° C. for extension (see PCR primer sets listed in Table 1). Expected sizes of the PCR products were 417 bp for IL2RG and 426 bp for RAG2. The PCR products were sequenced to identify the presence of indels.

Example 2: Somatic Cell Nuclear Transplantation

To produce SCNT embryos, sow-derived oocytes were purchased from ART (Madison, Wis.). The oocytes were shipped overnight in maturation medium (TCM199 with 2.9 mM Hepes, 5 µg/ml insulin, 10 ng/ml EGF, 0.5 µg/ml p-FSH, 0.91 mM pyruvate, 0.5 mM cysteine, 10% porcine follicular fluid, 25 ng/ml gentamicin) and transferred into fresh medium after 24 hours. After 40-42 hour of maturation, cumulus cells were removed from the oocytes by vortexing in the presence of 0.1% hyaluronidase. During manipulation, oocytes were placed in the manipulation medium supplemented with 7.0 µg/ml cytochalasin B. The polar body along with a portion of the adjacent cytoplasm, presumably containing the metaphase II plate, was removed and a donor cell was placed in the perivitelline space using a thin glass capillary. The reconstructed embryos were then fused in a fusion medium (0.3 M mannitol, 0.1 mM $CaCl_2$, 0.1 mM $MgCl_2$, 0.5 mM Hepes) by two DC pulses (1-sec interval) at 1.2 kV/cm for 30 sec using BTX Electro Cell Manipulator (Harvard Apparatus). After fusion, fused embryos were fully activated with 200 µM thimerosal for 10 min in the dark and 8 mM dithiothreitol for 30 min. Embryos were then incubated in Porcine Zygote Media 3 (PZM3)³ with 0.5 μM scriptaid, a histone deacetylase inhibitor, for 14-16 hours. The next day, the SCNT embryos were transferred into surrogates. For blastocysts transfers, the embryos were washed from the scriptaid and cultured for five additional days in PZM3 in the presence of 10 ng/ml CSF. SCNT embryos were surgically transferred into the ampullary-isthmic junction of a surrogate.

Example 3: Immunohistochemistry (IHC)

For IHC, tissues fixed in neutral buffer with 10% formalin were used. The tissues were embedded on slides for IHC. Endogenous peroxidase activity was first blocked in 3% hydrogen peroxidase. Samples were pretreated with Borg Decloaker, and then blocked in background Sniper solution. After washing, samples were incubated with primary antibodies either specific for B cells (CD79A; Diagnostic Biosystems—# Mob118, 1:100) or T cells (CD3; DAKO—# A0452, 1:400). After the incubation, samples were washed and incubated with HRP conjugated secondary antibodies. Samples were then stained with Romulin Red Chromogens to visualize the signal. Samples were also stained with IP FLX Hematoxylin to provide backgrounds. The Borg, Sniper, Romulin Red and IP FLX hematoxylin were all purchased from Biocare (Concord, Calif.). All photomicrographs were acquired using a Zeiss Axiophot microscope (Carl Zeiss, Oberkochen, Germany) equipped with an Olympus DP70 high-resolution digital microscope camera (Olympus, Center Valley, Pa.).

Example 4: Flow Cytometry

Portions of the spleen from freshly euthanized wildtype and biallelic piglets were collected into RPMI-1640 medium (Mediatech, Inc., Manassas, Va.) supplemented with 10% fetal bovine serum, minced with a scalpel blade, aspirated multiple times through a 20 ga. needle, and then forced through a 70 m nylon mesh cell strainer (BD Biosciences, San Jose, Calif.). The splenocyte suspension was then incubated for 15 minutes with Pharm Lyse solution (BD Biosciences) to lyse erythrocytes and then pelleted at 200×g for five minutes. After discarding the supernatant, the pellet was resuspended in cold staining buffer (BD Pharmingen) and cells were counted on a hemacytometer. Cells were then divided into aliquots of $5 \times 10^6$ cells in 200 μL staining buffer. The FITC-attached mouse anti-pig CD21, mouse anti-pig CD 3ε, and mouse anti T-2 mycotoxin IgG1k (Isotype control group) (SouthernBiotech, Birmingham, Ala.) were added to the cells to be 0.5 μg/$1 \times 10^6$ cells, and then, cultured at 4° C. in the dark condition. Cells were then washed twice and resuspended in fresh staining buffer. Cells were analyzed at the University of Missouri Cell and Immunobiology Core Facility using a CyAn ADP flow cytometer (Beckman Coulter, Brea, Calif.). Data were analyzed using Summit v4.3 software (Beckman Coulter).

Example 5: Off-Target Analysis

To identify putative off target sequences from the TALENs used in the present invention, bioinformatics tools were used to identify similar sequences to each TALEN binding site from the most recent pig genome assembly (Sscrofa10.2). PCR primers were designed flanking the most likely off target sites based on the number of nucleotide differences. These regions were amplified in the founder animals and tested for off-targeting events using the Surveyor nuclease assay (Tables 2 and 3). After PCR amplification, 300 to 500 ng of the PCR products (10 to 15 μl) was transferred into a fresh tube, and then, denaturated and annealed according to a thermocycler program (95° C. for 2 min, 95° C. to 85° C.-2° C. per second, 85° C. to 25° C.-0.1° C. per second, 4° C. indefinitely). 1 lie of Surveyor nuclease and 1 μl of Surveyor enhancer were added thereto, and then, incubated at 42° C. for 30 minutes. Then the reactions were immediately placed on ice and 6× Surveyor nuclease stop buffer and 6× dye were added to the reactions. The samples are electrophoresed on a 2.0% agarose gel.

Example 6: TUNEL Assay

Tissues were fixed in 4% (w/v) paraformaldehyde in 0.01 M PBS (pH 7.4), washed inPBS, dehydrated in ethanol (70%, 90%, and 100%) and embedded in paraffin wax. The sections (6 μm) were rehydrated (xylene 5 min; ethanol 100%, 95%, 70%, 2 min each) and washed in distilled water prior to TUNEL staining. The sections were incubated for 30 min with proteinase K (20 ㎕/ml in 10 mM Tris/HCl, pH 7.5) at room temperature. Sections were incubated for 10 min at room temperature in a moist chamber with the TUNEL mix (In situ Cell Death Detection kit, Roche, Swiss). After three PBS washes, slides were mounted in VECTASHIELD Mounting Media with DAPI (VECTOR, USA).

Example 7: Cellular Proliferation Assay

Cellular proliferation of fibroblast cells derived from wild-type, RAG2 monoalleic, and RAG2 biallelic pigs was measured by counting number of cells in culture after 24 h and 48 h. The cells were seeded at $1 \times 10^4$ cells/well on 12-well plates coated with laminin. The number of cells in each well was counted at 0, 24, and 48 h. Cells were stained with 0.4% trypan blue dye (Bio-Rad) to verify their viability. The number of cells at each time point were measured by using TC10 automated cell counter (Bio-Rad); three independent samples from each pig were used. Differences in the numbers of cells at 24 and 48 h were compared by using the Statistical Analysis System (SAS Institute, Cary, N.C.).

Example 8: Derivation of Human Umbilical Cord Fibroblasts

Human umbilical cord tissues were collected freshly and aseptically in University Hospital (University of Missouri, Columbia, Mo.). The tissue collection (project #1201132) has been approved by the University of Missouri Health Sciences Institutional Review Board. The tissues were washed twice or more with phosphate buffered saline (PBS) to remove blood cells and minced into 1? mm3 fragments with scissors in DMEM medium to deliver adherent cells by the explants method. The fragmented tissues were placed into a 48-well plate (one piece per well) coated with 0.1% gelatin in DMEM medium (Thermo) containing 10% FBS, 1% Non Essential Amino Acids, 2 mM glutamine, 0.1 mM 2-mercaptoethanol and 4 ng/ml FGF2, followed by culturing in an incubator containing a humidified atmosphere of 4% $02/5\% CO_2/91\% N_2$ at 37° C. The cultures were kept undisturbed for the first 5-7 days and supplemented with Primocin (InvivoGen, San Diego, Calif.) to reduce risk of bacterial and fungal growth in the primary culture. The medium without Primocin or other antibiotics was refreshed every two days thereafter until the fibroblastic adherent cells from the tissue fragments developed outgrowths in the wells. The fibroblasts outgrowths started appearing at the periphery of the minced tissues after a week of culture. By 10-11 days, the fibroblasts were passaged from the 48-well plate into T25 flasks by using TrypLE (Invitrogen). The cells reached confluence in the flask by ~14 days and were expanded for reprogramming to iPSC.

Example 9: Generation of iPSCs from Umbilical Cord Fibroblasts with Episomal Vectors A protocol developed by Okita et al with episomal vectors carrying shRNA for p53 suppression and nontransforming L-MYC, in addition to the usual reprogramming genes POU5F1, SOX2, KLF4 and LIN-28, was employed to reprogram the fibroblasts. Three micrograms of Y4 combination of the episomal plasmids was electroporated into $6\times10^5$ cells with a Nucleofector II device (Lonza, Basel, Switzerland) and Amaxa NHDF Nucleofector kit (Lonza) according to the manufacturer's instructions. An electroporation program 'U-020' in the device was used. The cells were allowed to recover for 2 to 4 days by culturing in the above conditions. Cells ($2\times10^5$) were placed into 100 mm dishes previously coated with Matrigel (BD Bioscience, San Jose, Calif.). The following day the culture medium was switched to mTeSR1 (StemCell Technologies, Vancouver, Canada). Colonies resembling human ESC emerged around 14 days post-transduction and the colonies were mechanically isolated around day 20 and expanded into feeder-free condition on a Matrigel substratum.

Example 10: Immunohistochemical Examination of iPSC

Images of iPSC were captured with an Olympus CKX41 inverted microscope equipped with a digital camera Coolpix 5000 (Nikon, Melville, N.Y.). For immunofluorescent analysis, cells were grown on coverslips coated with Matrigel. After fixation in 4% paraformaldehyde/PBS for 10 min and permeabilization in 1.0% Triton X-100/PBS for 30 min, coverslips were placed in 5% goat serum/5% BSA in PBS for 1 h. Next, the cells were incubated overnight at 4° C. with appropriately diluted primary antibodies, POU5F1 (1:200, sc-5279, Santa Cruz Biotechnology), NANOG (1:100, ab109250, Abcam), and SSEA4 (1:100, #4755p, Cell Signaling Technology) and followed by incubation with Alexa Fluor 568 or 488-labeled goat anti-mouse or rabbit antibody (1:500), Images were captured with an Olympus IX70 inverted microscope equipped with an ORCA-AG CCD camera (http://www.biotech.missouri.edu/mcc/Olympus.html).

Example 11: Teratoma Formation

Two Human iPSC lines (passage numbers between 4 and 9) from two individuals were injected (5 or 10 million cells per site) in 0.2 ml volume with 25% Matrigel solution subcutaneously into five pigs, 3 of them with a biallelic RAG2 modification and 2 with monoallelic modification of RAG2 as a control on day 1. The cultured iPSC were detached by dispase (StemCell Technologies) and scraping. After centrifugation (200×g, 5 min), the cell pellet was resuspended with 0.1 ml of mTeSR1 medium and mixed with same volume of 50% Matrigel. The cells were then chilled on ice and loaded into a 1 ml syringe (BD, Franklin Lakes, N.J.) and injected into two sites per pig, one ear and one lateral flank, through 22 gauge needles. The subsequent tumors were dissected out and fixed in 10% (v/v) neutral buffered formalin. Paraffin-embedded tissue was sectioned and then stained with hematoxylin and eosin (H&E). Porcine cells expressing trophoblast phenotypes generated from porcine iPSC (iTR) were transplanted to one of the biallelic RAG2 mutant pig. Ten million cells of the iTR subtype line (p29) were detached by TrypLE and scraping. The cell suspension was prepared as human iPSC and injected subcutaneously in the left ear. The cell transplant procedures were conducted in a blind format, with the individual performing the procedures unaware of the genetic status of the pigs.

Example 12: Immunohistochemical Analysis of Teratomas

For immunohistochemistry (IHC), tissues were fixed in 10% formalin in neutral buffer (Fisher, 99-909-14), embedded in paraffin, and sections (5 μm) prepared on glass slides. Endogenous peroxidase activity was first blocked by treating the tissues sections in 3% hydrogen peroxidase for an hour. Then the samples were pretreated with Borg Decloaker (Biocare Medical, Calif.) solution for antigen retrieval, and then blocked in Background Sniper (Biocare Medical, Calif.) solution. After washing, samples were incubated with primary antibodies (Table 4). After incubation, samples were washed and incubated with horse radish peroxidase (HRP) conjugated secondary antibodies. The EnVision™+ system (Dako, Carpinteria, Calif.) was employed for detection. Either 3, 3-diaminobenzicine (DAB) or Romulin AEC Chromogen (Biocare Medical, Concord, Calif.) was used to visualize the signal. The samples were also stained with IP FLX hematoxylin to provide background. All photomicrographs were acquired by using a Zeiss Axiophot microscope (Carl Zeiss, Oberkochen, Germany) equipped with an Olympus DP70 high-resolution digital microscope camera (Olympus, Center Valley, Pa.). The Borg, Sniper, Romulin Red and IP FLX hematoxylin were all purchased from Biocare (Concord, Calif.).

Example 13: Source of the Teratoma

To identify the source of teratomas, the human specific mitochondrial mitofusin 1 gene (MFN1) was amplified by using PCR. Genomic DNA was isolated from human iPSC, the teratomas, and blood from the tail of the RAG2 mutant pig carrying the teratoma by using a DNeasy Blood and Tissue kit (Qiagen, USA). Conditions for the PCR amplification was initial denaturation of for 2 min at 96° C. followed by 32 cycles of 30 sec at 95° C. for denaturation, 30 sec at 52° C. for annealing, and 30 min at 72° C. for extension. Products from the PCR were loaded on 2.5% agarose gel. Expected size of the PCR products was 236 bp. Primers for the analysis were F: GCTGGCTAAGAAGGCGATTA (SEQ ID NO. 2) and R: TCCCCTTCTGGAGGTTAGAAA (SEQ ID NO. 3).

TABLE 1

| GENE | Primer | product |
|---|---|---|
| RAG2 | F: AAGGATTCCTGCTACCTTCCTCCT (SEQ ID NO. 4) R: AGATAGCCCATCTTGAAGTTCTGG (SEQ ID NO. 5) | 426 |

TABLE 2

| Gene | Abbreviation | Primer | Product |
|---|---|---|---|
| Mannosidase 2, alpha 1 | MAN2A1 | F: TGCCACATGATGCCTTTCTA (SEQ ID NO. 6)<br>R: TGCTGGTTCAAGATGCTGTC (SEQ ID NO. 7) | 205 |
| Family with sequence similarity 82, member A2 | FAM82A | F: CCTAGGCCTGAGTGTGGGTA (SEQ ID NO. 8)<br>R: GCCCTGACGCTTTTATTCTG (SEQ ID NO. 9) | 194 |
| Metadherin | MTDH | F: TCCTTGCTTCCCTTGACTGT (SEQ ID NO. 10)<br>R: CGAGAGCATTTCTCGTAGCC (SEQ ID NO. 11) | 155 |
| Tripartite motif-containing 31 | TRIM31 | F: TGTGCAGTTTTCAACCATCC (SEQ ID NO. 12)<br>R: GTCTTTCAGTCCCCCTTTCC (SEQ ID NO. 13) | 163 |
| Proprotein convertase subtilisin/kexin type 2 | PCSK2 | F: ACAAGTGGCCTTTCATGACC (SEQ ID NO. 14)<br>R: CTCTTCCTCCAGCTCCTCCT (SEQ ID NO. 15) | 218 |
| Protein kinase, cAMPdependent, catalytic, beta | PRKACB | F: CACTAAATAGTGGCCTTCTTGGA (SEQ ID NO. 16)<br>R: ACACACCCATCCTTTTCCAG (SEQ ID NO. 17) | 352 |
| GC-rich sequence DNAbinding factor 2 | GCFC2 | F: GAAATGGGTTTGTTGAGTCCA (SEQ ID NO. 18)<br>R: ACGGTGGCAGAGCTGAATAG (SEQ ID NO. 19) | 417 |

Table 2 shows the primer set used for identifying off-site targeting of pig RAG2.

TABLE 3

| Cell types | Number of produced(transferred) embryos | Piglets born alive (still born) |
|---|---|---|
| RAG2 #14 (♂) | 248 (243) | 6(2) |
| RAG2 #14 (♂) | 180 (180) | 3(1) |
| RAG2 #12, 14 (♂) | 95 (48) | 6 |
| RAG2 #32 (♀) | 259 (249) | Day96 pregnant |
| RAG2 #32 (♀) | 262 (252) | Day95 pregnant |
| RAG2 #32 (♀) | 260 (250) | Day89 pregnant |

Table 3 shows the nuclear transplantation efficiencies according to the present invention.

TABLE 4

| Antigen Targeted | Source | Dilution |
|---|---|---|
| CD79A | Diagnostic Biosystems-# Mob118 | 1:100 |
| CD3 | DAKO-# A0452 | 1:400 |
| CD335 | Bioss-#bs-2417R | 1:100 |
| CD34 | Leica -#PA0212 | Prediluted |
| CD45 | Leica -#PA0042 | Prediluted |
| GFAP | Leica -#PA0026 | Prediluted |
| ENO2 | Leica-#PA0435 | Prediluted |
| CTNNB1 | Leica-#PA0083 | Prediluted |
| VWF | DAKO-#A0082 | 1:100 |
| ACTG2 | Leica-#PA0943 | Prediluted |
| DES | Leica-#PA0032 | Prediluted |
| CD 204 | Transgenic Inc - #KT022 | 1:100 |

Table 4 is antibodies used for IHC.

[Accession No.]

Name of Accession Organization: Korea Research Institute of Bioscience and Biotechnology Accession No.: KCTC 12496

Accession Date: 20131002

---

The invention claimed is:

1. A method for producing severe combined immunodeficiency (SCID)-like miniature pigs having a recombination activating gene (RAG) 2-allelic mutation, the method comprising:
    inducing an allelic mutation in a pig RAG 2 gene by exposing the gene to a transcription activator-like effector nuclease (TALEN) that recognizes a TALEN-recognizing sequence region as set forth in SEQ ID NO. 1 in Chromosome 2 of the pig;
    producing mutant embryos by using cells comprising the induced allelic mutation, wherein the producing is performed by somatic cell nuclear transplantation (SCNT); and
    transferring the embryos to a surrogate gilt and allowing the embryos to gestate to term.

2. The method of claim 1, wherein the method is performed by transfecting relevant cells using the TALEN in a vector encoding a TAL effector-DNA nuclease.

3. A SCID-like miniature pig having a recombination activating gene (RAG) 2-allelic mutation produced by the method of claim 1, wherein the RAG 2 allelic mutation is monoallelic or biallelic, and wherein the RAG 2 allelic mutation is RAG2+/Δ140, S141H or RAG2+/Δ140, S141H/Δ140-527.

4. A method for sorting cells having an allelic mutation in a recombination activating gene (RAG) 2 gene, the method comprising:
    introducing to the cells a vector encoding a TAL effector-DNA nuclease capable of inducing one or more mutations in a TALEN-recognizing sequence region as set forth in SEQ ID NO. 1 in Chromosome 2 of a pig or surrounding sites thereof, and a reporter vector encoding a gene encoding a red fluorescent protein (RFP), a gene encoding a green fluorescent protein (GFP), a targeting sequence as set forth in SEQ ID NO. 1, and a H-2KK gene, and
    sorting the cells based on presence of the reporter vector.

5. The method of claim 4, wherein expression of H-2KK is detected by an antibody.

6. The method of claim 4, wherein expression of RFP and GFP are detected by flow cytometry.

7. A cell comprising an induced RAG 2 allelic mutation, wherein the RAG 2 allelic mutation is monoallelic or biallelic, and wherein the RAG 2 allelic mutation is RAG2+/Δ140, S141H or RAG2+/Δ140, S141H/Δ140-527.

8. The cell of claim 7, wherein the cell is from a RAG2-knockout miniature pig fibroblast cell line, accession number KCTC 12496.

9. The method of claim 1, wherein the pig is a pig of species *Sus scrofa*.

10. The method of claim 4, wherein the pig is a pig of species *Sus scrofa*.

* * * * *

SEQUENCE LISTING

<160> NUMBER OF SEQ ID NOS: 42

<210> SEQ ID NO 1
<211> LENGTH: 52
<212> TYPE: DNA
<213> ORGANISM: Sus scrofa

```
<400> SEQUENCE: 1
ttcctgaagg cagatatggt cattccattg atgtcgtgta tagtcgaggg aa        52

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctggctaag aaggcgatta                                             20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccccttctg gaggttagaa a                                           21

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaggattcct gctaccttcc tcct                                        24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agatagccca tcttgaagtt ctgg                                        24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgccacatga tgcctttcta                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
tgctggttca agatgctgtc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctaggcctg agtgtgggta                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccctgacgc ttttattctg                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tccttgcttc ccttgactgt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgagagcatt tctcgtagcc                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgtgcagttt tcaaccatcc                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 13
gtctttcagt cccccttttcc                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acaagtggcc tttcatgacc                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcttcctcc agctcctcct                                                 20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cactaaatag tggccttctt gga                                             23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acacacccat cctttccag                                                  20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaaatgggtt tgttgagtcc a                                               21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acggtggcag agctgaatag                                                          20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atgttcctga aggcagatat ggt                                                      23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgtcgtgtat agtcgaggga aaag                                                     24

<210> SEQ ID NO 22
<211> LENGTH: 49
<212> TYPE: DNA
<213> ORGANISM: Sus scrofa

<400> SEQUENCE: 22
ttcctgaagg cagatatggt cccattgatg tcgtgtatag tcgagggaa                          49

<210> SEQ ID NO 23
<211> LENGTH: 38
<212> TYPE: DNA
<213> ORGANISM: Sus scrofa

<400> SEQUENCE: 23
ttcctgaagg cagatatggt cgtgtatagt cgagggaa                                      38

<210> SEQ ID NO 24
<211> LENGTH: 52
<212> TYPE: DNA
<213> ORGANISM: Sus scrofa

<400> SEQUENCE: 24
ttcctgaagg cagatatggt cattccattg atgtcgtgta tagtcgaggg aa                      52

<210> SEQ ID NO 25
<211> LENGTH: 52
<212> TYPE: DNA
<213> ORGANISM: Sus scrofa

<400> SEQUENCE: 25
ttcctggagg cagatatggt tgtccctggg gagtccccccc agaaacaatt ta                     52

<210> SEQ ID NO 26
<211> LENGTH: 52
<212> TYPE: DNA
<213> ORGANISM: Sus scrofa

<400> SEQUENCE: 26
atcgttttca ctgattaata atattcaata ccaaagtata tagtctaaga tt                      52

```
<210> SEQ ID NO 27
<211> LENGTH: 52
<212> TYPE: DNA
<213> ORGANISM: Sus scrofa

<400> SEQUENCE: 27
cggcgtctgt gcgccccagc gtcatcccga gagtccccct dacgggaggg aa          52

<210> SEQ ID NO 28
<211> LENGTH: 52
<212> TYPE: DNA
<213> ORGANISM: Sus scrofa

<400> SEQUENCE: 28
gtgctacaat aaatagtctt gtgtggagtt ttgtcgtgta tttgaaactt tc          52

<210> SEQ ID NO 29
<211> LENGTH: 52
<212> TYPE: DNA
<213> ORGANISM: Sus scrofa

<400> SEQUENCE: 29
gtgctgaagg agtggacgct gatgctgcac ggcacgcaga gcgcccctta ca          52

<210> SEQ ID NO 30
<211> LENGTH: 52
<212> TYPE: DNA
<213> ORGANISM: Sus scrofa

<400> SEQUENCE: 30
atagtaaagg cagaacctgg acattatgtg gcactccaga atatttggct cc          52

<210> SEQ ID NO 31
<211> LENGTH: 52
<212> TYPE: DNA
<213> ORGANISM: Sus scrofa

<400> SEQUENCE: 31
ccaagaaaga cagttctggt caggtctaaa ggtaagcaga aaactgccaa aa          52

<210> SEQ ID NO 32
<211> LENGTH: 23
<212> TYPE: DNA
<213> ORGANISM: Sus scrofa

<400> SEQUENCE: 32
cagatatggt cattccattg atg                                         23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
```

-continued

```
<400> SEQUENCE: 33
cagatatggt cccnttnatg tcn                                          23

<210> SEQ ID NO 34
<211> LENGTH: 139
<212> TYPE: PRT
<213> ORGANISM: Sus scrofa

<400> SEQUENCE: 34

Met Ser Leu Gln Met Ile Thr Val Gly Asn Asn Met Ala Leu Ile Gln
1               5                   10                  15

Pro Gly Phe Ser Leu Met Asn Phe Asp Gly Gln Ile Phe Phe Phe Gly
            20                  25                  30

Gln Lys Gly Trp Pro Lys Arg Ser Cys Pro Thr Gly Val Phe His Phe
        35                  40                  45

Asp Val Lys His Asn His Leu Lys Leu Lys Pro Ala Leu Phe Ser Lys
    50                  55                  60

Asp Ser Cys Tyr Leu Pro Pro Leu Arg Tyr Pro Ala Thr Cys Thr Phe
65                  70                  75                  80

Lys Ser Ser Leu Glu Ser Glu Lys His Gln Tyr Ile Ile His Gly Gly
                85                  90                  95

Lys Thr Pro Asn Asn Glu Leu Ser Asp Lys Ile Tyr Val Met Ser Val
            100                 105                 110

Val Cys Lys Asn Asn Lys Lys Val Thr Phe Arg Cys Arg Glu Lys Asp
        115                 120                 125

Leu Val Gly Asp Val Pro Glu Gly Arg Tyr Gly
    130                 135

<210> SEQ ID NO 35
<211> LENGTH: 526
<212> TYPE: PRT
<213> ORGANISM: Sus scrofa

<400> SEQUENCE: 35

Met Ser Leu Gln Met Ile Thr Val Gly Asn Asn Met Ala Leu Ile Gln
1               5                   10                  15

Pro Gly Phe Ser Leu Met Asn Phe Asp Gly Gln Ile Phe Phe Phe Gly
            20                  25                  30

Gln Lys Gly Trp Pro Lys Arg Ser Cys Pro Thr Gly Val Phe His Phe
        35                  40                  45

Asp Val Lys His Asn His Leu Lys Leu Lys Pro Ala Leu Phe Ser Lys
    50                  55                  60

Asp Ser Cys Tyr Leu Pro Pro Leu Arg Tyr Pro Ala Thr Cys Thr Phe
65                  70                  75                  80

Lys Ser Ser Leu Glu Ser Glu Lys His Gln Tyr Ile Ile His Gly Gly
                85                  90                  95

Lys Thr Pro Asn Asn Glu Leu Ser Asp Lys Ile Tyr Val Met Ser Val
            100                 105                 110

Val Cys Lys Asn Asn Lys Lys Val Thr Phe Arg Cys Arg Glu Lys Asp
        115                 120                 125

Leu Val Gly Asp Val Pro Glu Gly Arg Tyr Gly Pro Ile Asp Val Val
    130                 135                 140

Tyr Ser Arg Gly Lys Ser Met Gly Val Leu Phe Gly Gly Arg Ser Tyr
145                 150                 155                 160

Ile Pro Ser Ala Gln Arg Thr Thr Glu Lys Trp Asn Ser Val Ala Asp
                165                 170                 175
```

Cys Leu Pro His Ile Phe Leu Val Asp Phe Glu Phe Gly Cys Ser Thr
                180                 185                 190

Ser Tyr Ile Leu Pro Glu Leu Gln Asp Gly Leu Ser Phe His Val Ser
            195                 200                 205

Ile Ala Arg Asn Asp Thr Ile Tyr Ile Leu Gly Gly His Ser Leu Ala
        210                 215                 220

Asn Asn Ile Arg Pro Ala Asn Leu Tyr Lys Ile Arg Val Asp Leu Pro
225                 230                 235                 240

Leu Gly Ser Pro Ala Val Thr Cys Thr Val Leu Pro Gly Gly Ile Ser
                245                 250                 255

Val Ser Ser Ala Ile Leu Thr Gln Thr Ser Ser Asp Glu Phe Val Ile
            260                 265                 270

Val Gly Gly Tyr Gln Leu Glu Asn Gln Lys Arg Met Val Cys Asn Ile
        275                 280                 285

Ile Ser Phe Lys Asp Asn Lys Ile Gly Ile His Glu Met Glu Thr Pro
        290                 295                 300

Asp Trp Thr Pro Asp Ile Lys His Ser Lys Ile Trp Phe Gly Ser Asn
305                 310                 315                 320

Met Gly Asn Gly Thr Val Phe Leu Gly Ile Pro Gly Asp Asn Lys Gln
                325                 330                 335

Ala Leu Ser Glu Ala Phe Tyr Phe Tyr Thr Leu Lys Cys Thr Glu Asp
            340                 345                 350

Asp Val Asn Glu Asp Gln Lys Thr Phe Thr Asn Ser Gln Thr Ser Thr
        355                 360                 365

Glu Asp Pro Gly Asp Ser Thr Pro Phe Glu Asp Ser Glu Glu Phe Cys
370                 375                 380

Phe Ser Ala Glu Ala Asn Ser Phe Asp Gly Asp Asp Glu Phe Asp Thr
385                 390                 395                 400

Tyr Asn Glu Asp Asp Glu Asp Glu Ser Glu Thr Gly Tyr Trp Ile
                405                 410                 415

Thr Cys Cys Pro Thr Cys Asp Met Asp Ile Asn Thr Trp Val Pro Phe
            420                 425                 430

Tyr Ser Thr Glu Leu Asn Lys Pro Ala Met Ile Tyr Cys Ser His Gly
        435                 440                 445

Asp Gly His Trp Val His Ala Gln Cys Met Asp Leu Ala Glu His Thr
    450                 455                 460

Leu Ile His Leu Ser Glu Gly Ser Ser Lys Tyr Tyr Cys Lys Glu His
465                 470                 475                 480

Val Glu Ile Ala Arg Ala Leu Gln Thr Pro Lys Arg Val Leu Pro Leu
                485                 490                 495

Lys Lys Pro Pro Leu Lys Ser Leu His Lys Lys Gly Ser Gly Lys Ile
            500                 505                 510

Ile Thr Pro Ala Lys Lys Ser Phe Leu Arg Arg Leu Phe Asp
        515                 520                 525

<210> SEQ ID NO 36
<211> LENGTH: 527
<212> TYPE: PRT
<213> ORGANISM: Sus scrofa

<400> SEQUENCE: 36

Met Ser Leu Gln Met Ile Thr Val Gly Asn Asn Met Ala Leu Ile Gln
1               5                   10                  15

Pro Gly Phe Ser Leu Met Asn Phe Asp Gly Gln Ile Phe Phe Phe Gly
            20                  25                  30

```
Gln Lys Gly Trp Pro Lys Arg Ser Cys Pro Thr Gly Val Phe His Phe
             35                  40                  45

Asp Val Lys His Asn His Leu Lys Leu Lys Pro Ala Leu Phe Ser Lys
 50                  55                  60

Asp Ser Cys Tyr Leu Pro Pro Leu Arg Tyr Pro Ala Thr Cys Thr Phe
 65                  70                  75                  80

Lys Ser Ser Leu Glu Ser Glu Lys His Gln Tyr Ile Ile His Gly Gly
                 85                  90                  95

Lys Thr Pro Asn Asn Glu Leu Ser Asp Lys Ile Tyr Val Met Ser Val
                100                 105                 110

Val Cys Lys Asn Asn Lys Lys Val Thr Phe Arg Cys Arg Glu Lys Asp
            115                 120                 125

Leu Val Gly Asp Val Pro Glu Gly Arg Tyr Gly His Ser Ile Asp Val
        130                 135                 140

Val Tyr Ser Arg Gly Lys Ser Met Gly Val Leu Phe Gly Gly Arg Ser
145                 150                 155                 160

Tyr Ile Pro Ser Ala Gln Arg Thr Thr Glu Lys Trp Asn Ser Val Ala
                165                 170                 175

Asp Cys Leu Pro His Ile Phe Leu Val Asp Phe Glu Phe Gly Cys Ser
            180                 185                 190

Thr Ser Tyr Ile Leu Pro Glu Leu Gln Asp Gly Leu Ser Phe His Val
        195                 200                 205

Ser Ile Ala Arg Asn Asp Thr Ile Tyr Ile Leu Gly Gly His Ser Leu
    210                 215                 220

Ala Asn Asn Ile Arg Pro Ala Asn Leu Tyr Lys Ile Arg Val Asp Leu
225                 230                 235                 240

Pro Leu Gly Ser Pro Ala Val Thr Cys Thr Val Leu Pro Gly Gly Ile
                245                 250                 255

Ser Val Ser Ser Ala Ile Leu Thr Gln Thr Ser Ser Asp Glu Phe Val
            260                 265                 270

Ile Val Gly Gly Tyr Gln Leu Glu Asn Gln Lys Arg Met Val Cys Asn
        275                 280                 285

Ile Ile Ser Phe Lys Asp Asn Lys Ile Gly Ile His Glu Met Glu Thr
    290                 295                 300

Pro Asp Trp Thr Pro Asp Ile Lys His Ser Lys Ile Trp Phe Gly Ser
305                 310                 315                 320

Asn Met Gly Asn Gly Thr Val Phe Leu Gly Ile Pro Gly Asp Asn Lys
                325                 330                 335

Gln Ala Leu Ser Glu Ala Phe Tyr Phe Tyr Thr Leu Lys Cys Thr Glu
            340                 345                 350

Asp Asp Val Asn Glu Asp Gln Lys Thr Phe Thr Asn Ser Gln Thr Ser
        355                 360                 365

Thr Glu Asp Pro Gly Asp Ser Thr Pro Phe Glu Asp Ser Glu Glu Phe
    370                 375                 380

Cys Phe Ser Ala Glu Ala Asn Ser Phe Asp Gly Asp Asp Glu Phe Asp
385                 390                 395                 400

Thr Tyr Asn Glu Asp Asp Glu Glu Asp Glu Ser Glu Thr Gly Tyr Trp
                405                 410                 415

Ile Thr Cys Cys Pro Thr Cys Asp Met Asp Ile Asn Thr Trp Val Pro
            420                 425                 430

Phe Tyr Ser Thr Glu Leu Asn Lys Pro Ala Met Ile Tyr Cys Ser His
        435                 440                 445
```

```
Gly Asp Gly His Trp Val His Ala Gln Cys Met Asp Leu Ala Glu His
    450                 455                 460

Thr Leu Ile His Leu Ser Glu Gly Ser Ser Lys Tyr Tyr Cys Lys Glu
465                 470                 475                 480

His Val Glu Ile Ala Arg Ala Leu Gln Thr Pro Lys Arg Val Leu Pro
                485                 490                 495

Leu Lys Lys Pro Pro Leu Lys Ser Leu His Lys Lys Gly Ser Gly Lys
            500                 505                 510

Ile Ile Thr Pro Ala Lys Lys Ser Phe Leu Arg Arg Leu Phe Asp
        515                 520                 525

<210> SEQ ID NO 37
<211> LENGTH: 160
<212> TYPE: PRT
<213> ORGANISM: Homo sapiens

<400> SEQUENCE: 37

Met Ser Leu Gln Met Val Thr Val Ser Asn Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Leu
        35                  40                  45

Asp Val Lys His Asn His Val Lys Leu Lys Pro Thr Ile Phe Ser Lys
    50                  55                  60

Asp Ser Cys Tyr Leu Pro Pro Leu Arg Tyr Pro Ala Thr Cys Thr Phe
65                  70                  75                  80

Lys Gly Ser Leu Glu Ser Glu Lys His Gln Tyr Ile Ile His Gly Gly
                85                  90                  95

Lys Thr Pro Asn Asn Glu Val Ser Asp Lys Ile Tyr Val Met Ser Ile
            100                 105                 110

Val Cys Lys Asn Asn Lys Lys Val Thr Phe Arg Cys Thr Glu Lys Asp
        115                 120                 125

Leu Val Gly Asp Val Pro Glu Ala Arg Tyr Gly His Ser Ile Asn Val
    130                 135                 140

Val Tyr Ser Arg Gly Lys Ser Met Gly Val Leu Phe Gly Gly Arg Ser
145                 150                 155                 160

<210> SEQ ID NO 38
<211> LENGTH: 160
<212> TYPE: PRT
<213> ORGANISM: Macaca mulatta

<400> SEQUENCE: 38

Met Ser Leu Gln Met Val Thr Val Ser Asn Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Leu
        35                  40                  45

Asp Val Lys His Asn His Val Lys Leu Lys Pro Thr Ile Phe Ser Lys
    50                  55                  60

Asp Ser Cys Tyr Leu Pro Pro Leu Arg Tyr Pro Ala Thr Cys Thr Phe
65                  70                  75                  80

Lys Gly Asn Leu Glu Ser Glu Lys His Gln Tyr Ile Ile His Gly Gly
                85                  90                  95
```

```
Lys Thr Pro Asn Asn Glu Leu Ser Asp Lys Ile Tyr Val Met Ser Ile
            100                 105                 110

Val Cys Lys Asn Lys Arg Val Thr Phe Arg Cys Thr Glu Lys Asp
        115                 120                 125

Leu Val Gly Asp Val Pro Glu Ala Arg Tyr Gly His Ser Ile Asn Val
    130                 135                 140

Val Tyr Ser Arg Gly Lys Ser Met Gly Val Leu Phe Gly Gly Arg Ser
145                 150                 155                 160

<210> SEQ ID NO 39
<211> LENGTH: 160
<212> TYPE: PRT
<213> ORGANISM: Bos taurus

<400> SEQUENCE: 39

Met Ser Leu Gln Met Val Thr Val Gly Asn Ser Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Phe
        35                  40                  45

Glu Val Lys His Asn His Leu Lys Leu Lys Pro Ala Val Phe Ser Lys
    50                  55                  60

Asp Ser Cys Tyr Leu Pro Pro Leu Arg Tyr Pro Ala Thr Cys Thr Phe
65                  70                  75                  80

Ser Gly Asn Leu Glu Ser Glu Lys His Gln Tyr Ile Ile His Gly Gly
                85                  90                  95

Lys Thr Pro Asn Asn Glu Leu Ser Asp Lys Ile Tyr Val Met Ser Val
            100                 105                 110

Val Ser Lys Asn Asn Lys Val Thr Phe Arg Cys Thr Glu Lys Asp
        115                 120                 125

Leu Val Gly Asp Ile Pro Glu Gly Arg Tyr Gly His Ser Ile Asp Val
    130                 135                 140

Val Tyr Ser Arg Gly Lys Ser Met Gly Val Leu Phe Gly Gly Arg Ser
145                 150                 155                 160

<210> SEQ ID NO 40
<211> LENGTH: 160
<212> TYPE: PRT
<213> ORGANISM: Mus musculus

<400> SEQUENCE: 40

Met Ser Leu Gln Met Val Thr Val Gly His Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Phe
        35                  40                  45

Asp Ile Lys Gln Asn His Leu Lys Leu Lys Pro Ala Ile Phe Ser Lys
    50                  55                  60

Asp Ser Cys Tyr Leu Pro Pro Leu Arg Tyr Pro Ala Thr Cys Ser Tyr
65                  70                  75                  80

Lys Gly Ser Ile Asp Ser Asp Lys His Gln Tyr Ile Ile His Gly Gly
                85                  90                  95

Lys Thr Pro Asn Asn Glu Leu Ser Asp Lys Ile Tyr Ile Met Ser Val
            100                 105                 110
```

```
Ala Cys Lys Asn Asn Lys Lys Val Thr Phe Arg Cys Thr Glu Lys Asp
            115                 120                 125

Leu Val Gly Asp Val Pro Glu Pro Arg Tyr Gly His Ser Ile Asp Val
        130                 135                 140

Val Tyr Ser Arg Gly Lys Ser Met Gly Val Leu Phe Gly Gly Arg Ser
145                 150                 155                 160

<210> SEQ ID NO 41
<211> LENGTH: 160
<212> TYPE: PRT
<213> ORGANISM: Gallus gallus

<400> SEQUENCE: 41

Met Ser Leu Gln Met Val Ser Ala Val Ser Asn Ser Ser Leu Leu Gln
1               5                   10                  15

Pro Gly Ser Ser Leu Leu Asn Phe Asp Gly His Val Phe Phe Phe Gly
            20                  25                  30

Gln Lys Gly Trp Pro Lys Arg Ser Cys Pro Thr Gly Val Phe Phe Leu
        35                  40                  45

Asp Ile Lys Gln Asn Glu Leu Lys Met Lys Pro Ala Ala Phe Ser Arg
    50                  55                  60

Asp Ser Cys Tyr Leu Pro Pro Leu Arg Tyr Pro Ala Ile Cys Thr Leu
65                  70                  75                  80

Arg Gly Asn Gly Glu Ser Asp Lys His Gln Tyr Ile Ile His Gly Gly
                85                  90                  95

Lys Thr Pro Asn Asn Asp Leu Ser Asp Lys Ile Tyr Ile Met Ser Met
            100                 105                 110

Val Asn Lys Thr Thr Lys Lys Thr Thr Phe Gln Cys Ile Glu Lys Asp
        115                 120                 125

Leu Gly Gly Asp Val Pro Glu Ala Arg Tyr Gly His Thr Ile Asn Val
    130                 135                 140

Val His Ser Arg Gly Lys Ser Met Ile Val Ile Phe Gly Gly Arg Ser
145                 150                 155                 160

<210> SEQ ID NO 42
<211> LENGTH: 160
<212> TYPE: PRT
<213> ORGANISM: Sus scrofa

<400> SEQUENCE: 42

Met Ser Leu Gln Met Ile Thr Val Gly Asn Asn Met Ala Leu Ile Gln
1               5                   10                  15

Pro Gly Phe Ser Leu Met Asn Phe Asp Gly Gln Ile Phe Phe Phe Gly
            20                  25                  30

Gln Lys Gly Trp Pro Lys Arg Ser Cys Pro Thr Gly Val Phe His Phe
        35                  40                  45

Asp Val Lys His Asn His Leu Lys Leu Lys Pro Ala Leu Phe Ser Lys
    50                  55                  60

Asp Ser Cys Tyr Leu Pro Pro Leu Arg Tyr Pro Ala Thr Cys Thr Phe
65                  70                  75                  80

Lys Ser Ser Leu Glu Ser Glu Lys His Gln Tyr Ile Ile His Gly Gly
                85                  90                  95

Lys Thr Pro Asn Asn Glu Leu Ser Asp Lys Ile Tyr Val Met Ser Val
            100                 105                 110

Val Cys Lys Asn Asn Lys Lys Val Thr Phe Arg Cys Arg Glu Lys Asp
        115                 120                 125
```

```
Leu Val Gly Asp Val Pro Glu Gly Arg Tyr Gly His Ser Ile Asp Val
    130                 135                 140
Val Tyr Ser Arg Gly Lys Ser Met Gly Val Leu Phe Gly Gly Arg Ser
145                 150                 155                 160
```